United States Patent
Peyman

(10) Patent No.: US 7,037,943 B2
(45) Date of Patent: May 2, 2006

(54) RETINAL TREATMENT METHOD

(75) Inventor: Gholam Peyman, New Orleans, LA (US)

(73) Assignee: Optobionics Corporation, Naperville, IL (US)

(*) Notice: Subject to any disclaimer, the term of this patent is extended or adjusted under 35 U.S.C. 154(b) by 577 days.

(21) Appl. No.: 09/832,269

(22) Filed: Apr. 10, 2001

(65) Prior Publication Data

US 2002/0147464 A1 Oct. 10, 2002

(51) Int. Cl.
*A61K 31/135* (2006.01)

(52) U.S. Cl. .................. 514/646; 514/652; 514/912; 424/427

(58) Field of Classification Search ................ 514/649, 514/652, 912, 27; 424/45
See application file for complete search history.

(56) References Cited

U.S. PATENT DOCUMENTS

| | | |
|---|---|---|
| 1,325,669 A | 12/1919 | Green |
| 2,760,483 A | 8/1956 | Tassicker |
| 3,594,823 A | 7/1971 | Collins |
| 3,628,193 A | 12/1971 | Collins |
| 3,766,311 A | 10/1973 | Boll |
| 3,848,608 A | 11/1974 | Leonard |
| 3,914,800 A | 10/1975 | Collins |
| 4,001,867 A | 1/1977 | Kravitz et al. |
| 4,211,474 A | 7/1980 | Le Goff |
| 4,251,887 A | 2/1981 | Anis |
| 4,272,910 A | 6/1981 | Danz |
| 4,551,149 A | 11/1985 | Sciarra |
| 4,600,004 A | 7/1986 | Lopez et al. |
| 4,601,545 A | 7/1986 | Kern |
| 4,628,933 A | 12/1986 | Michelson |
| 4,679,572 A | 7/1987 | Baker, Jr. |
| 4,681,102 A | 7/1987 | Bartell |
| 4,750,498 A | 6/1988 | Graham |
| 4,810,050 A | 3/1989 | Hooper |
| 4,832,202 A | 5/1989 | Newman et al. |
| 4,836,202 A | 6/1989 | Krasner |
| 4,873,448 A | 10/1989 | Shirai |
| 4,936,827 A | 6/1990 | Grimm et al. |
| 4,978,842 A | 12/1990 | Hinton et al. |
| 5,016,633 A | 5/1991 | Chow |
| 5,024,223 A | 6/1991 | Chow |
| 5,109,844 A | 5/1992 | de Juan, Jr. et al. |
| 5,130,528 A | 7/1992 | Phillips, Jr. |
| 5,130,776 A | 7/1992 | Popovic et al. |
| 5,159,927 A | 11/1992 | Schmid |
| 5,223,728 A | 6/1993 | Gempe |
| 5,256,882 A | 10/1993 | Miyasaka |
| 5,273,530 A | 12/1993 | Del Cerro et al. |
| 5,288,291 A | 2/1994 | Teoh |
| 5,338,991 A | 8/1994 | Lu |
| 5,351,309 A | 9/1994 | Lee et al. |
| 5,397,350 A | 3/1995 | Chow et al. |
| 5,411,540 A | 5/1995 | Edell et al. |
| 5,476,494 A | 12/1995 | Edell et al. |
| 5,484,403 A | 1/1996 | Yoakum et al. |
| 5,491,349 A | 2/1996 | Komoto et al. |
| 5,556,423 A | 9/1996 | Chow et al. |
| 5,648,655 A | 7/1997 | Rostoker |
| 5,676,679 A | 10/1997 | Simon et al. |
| 5,717,201 A | 2/1998 | Lin et al. |
| 5,814,017 A | 9/1998 | Kashmer |
| 5,817,075 A | 10/1998 | Giungo |
| 5,837,995 A | 11/1998 | Chow et al. |
| 5,865,839 A | 2/1999 | Doorish |
| 5,895,414 A | 4/1999 | Sanchez-Zambrano |
| 5,895,415 A | 4/1999 | Chow et al. |
| 5,930,937 A | 8/1999 | Bowersock |
| 5,935,155 A | 8/1999 | Humayun et al. |
| 5,941,250 A | 8/1999 | Aramant et al. |
| 5,944,747 A | 8/1999 | Greenberg et al. |
| 5,962,027 A | 10/1999 | Hughes |
| 6,032,062 A | 2/2000 | Nisch |
| 6,066,675 A | 5/2000 | Wen et al. ................ 514/649 |
| 6,159,218 A | 12/2000 | Aramant et al. |
| 6,035,236 A1 | 5/2001 | Jarding et al. |
| 6,230,057 B1 | 5/2001 | Chow et al. |
| 6,280,449 B1 | 8/2001 | Blake |
| 6,298,270 B1 | 10/2001 | Nisch et al. |
| 6,347,250 B1 | 2/2002 | Nisch et al. |
| 6,387,101 B1 | 5/2002 | Butts et al. |
| 6,389,317 B1 | 5/2002 | Chow et al. |
| 6,393,327 B1 | 5/2002 | Scribner |
| 6,427,087 B1 | 7/2002 | Chow et al. |
| 2002/0055724 A1 | 5/2002 | Hughes |
| 2002/0147464 A1 | 10/2002 | Peyman |

FOREIGN PATENT DOCUMENTS

| | | |
|---|---|---|
| DE | 195 29 371 C2 | 2/1997 |
| EP | 0 084 621 A2 | 11/1982 |
| EP | 0 233 789 | 8/1987 |
| EP | 0 501 904 A2 | 9/1992 |
| GB | 2 229 543 A | 9/1990 |
| WO | WO 99/15119 | 4/1999 |

OTHER PUBLICATIONS

Majii, Ajit, et al.: *Long–Term Histological and Electrophysiological Results of an Inactive Epiretinal Electrode Array Implantation in Dogs*, Investigative Ophthalmology & Visual Science, Aug. 1999, vol. 40, No. 9, pp. 2073–2081.

(Continued)

*Primary Examiner*—Zohreh Fay
(74) *Attorney, Agent, or Firm*—Brinks Hofer Gilson & Lione

(57) ABSTRACT

A method for treating or preventing retinal pathology or injury. The method locates and secures a retinal stimulating substance in the eye between the internal limiting membrane and the retina, which is the target site for the substance. The substance may be an implant that provides electrical stimulation to adjacent ganglion and neurofiber cells. Alternatively, the substance may be a pharmaceutical substance to stimulate the retina. In addition to providing direct contact of the substance with its target, the method obviates the need for artificial structures such as tacks or adhesives which may cause retinal bleeding or traction.

31 Claims, 1 Drawing Sheet

OTHER PUBLICATIONS

Margalit, e al: *Bioadhesives for Intraocular Use*, Retina, The Journal of Retinal and Vitreous Diseases, 2000, vol. 20, No. 5, pp. 469–477.

Peyman, Gholam, MD, et al.: *Subretinal Semiconductor Microphotodiode Array*, Opthalmic Surgery and Lasers, Mar. 1998, vol. 29, No. 3, pp 234–241.

Acheson, A., P.A. Barker, R.F. Alderson, F.D. Miller, et al., "Detection of Brain–Derived Neurotrophic Factor–Like Activity in Fibroblasts and Schwann Cells: Inhibition by Antibodies to NGF", Neuron, vol. 7, 1991, pp. 265–75.

Agnew, W.F. et al. Neural Prostheses Fundamental Studies, Englewood Cliffs, Prentice Hall, 1990, pp. 25–65.

Bosco, A., and Linden R., "BDNF and NT–4 Differentially Modulate Neurite Outgrowth in Developing Retinal Ganglion Cells", J Neurosci Res. vol. 57, 1999, pp 759–69.

Brady, G.S., Clauser, H.R., Materials Handbook, Thirteenth Edition, New York, McGraw–Hill, 1991, pp 739–740.

Caleo, M., Lodovichi, C., and Maffei, L., "Effects of Nerve Growth Factor on Visual Cortical Plasticity Require Afferent Electrical Activity", Eur. J. Neurosci., vol. 11, 1999, pp 2979–84.

Carmignoto, G., Maffei, L., Candeo, P., Canella, R. and Comelli, C., "Effect of NGF on the Survival of Rat Retinal Ganglion Cells Following Optic Nerve Section", J. Neurosci., vol. 9, 1989, pp 1263–72.

Chow, A.Y., Pardue, M.T., Chow, V.Y., Peyman, G.A., et al., "Implantation of Silicon Chip Microphotodiode Arrays into the Cat Subretinal Space", IEEE Trans. Neu. Syst. Rehabil. Eng., vol. 9, 2001, pp 86–95.

Chow, A.Y., and Chow, V.Y., "Subretinal Electrical Stimulation of the Rabbit Retina", Neurosci. Lett. vol. 225, 1997, pp 13–16.

Chow, A.Y., and Peachey, N., "The Subretinal Microphotodiode Array Retinal Prosthesis II", Ophthal. Res., vol. 31, 1999, p. 246.

Cui, Q., So, K.F., and Yip, H.K., "Major Biological Effects of Neurotrophic Factors on Retinal Ganglion Cells in Mammals", Biol. Sig. Recept., vol. 7, 1998, pp 220–226.

Dooley, D.M., Sharkey, J., Keller, W., and Kasprak, W., "Treatment of Demyelinating and Degenerative Diseases by Electro Stimulation of the Spinal Cord", Med. Prog. Technol., vol. 6, 1978, pp 1–14.

Evans, R.D., Foltz, D., and Foltz, K., "Electrical Stimulation with Bone and Wound Healing", *Clin. Podiatr. Med. Surg.*, vol. 18, 2001, pp 79–95.

Frasson, M., Picaud, S., Leveillard, T., Simonutti, M., et al., "Glial Cell Line–Derived Neurotrophic Factor Induces Histologic and Functional Protection of Rod Photoreceptors in the rd/rd Mouse", Invest. Ophthalmol. Visual Sci., vol. 40, 1999, pp 2724–34.

Klinke, R., Kral, A., Heid, S., Tillein, J., and Hartmann, R., "Recruitment of the Auditory Cortex in Congenitally Deaf Cats by Long–Term Cochlear Electrostimulation", Science, vol. 285, 1999, pp. 1729–1733.

Koyama, S., Haruyama, T. Kobatake, E., and Aizawa, M., "Electrically Induced NGF Production by Astroglial Cells", Nature Biotechnol., vol. 15, 1997, pp 164–166.

Lagey, C.L., Roelofs, J.M., Janssen, L.W.M., Breedijk, M., et al., "Electrical Stimulation of Bone Growth with Direct Current", Clin. Orthop., No. 204, 1986, pp 303–312.

Lambiase, A., and Aloe, L., "Nerve Growth Factor Delays Retinal Degeneration in C3H Mice", Graefe's Arch. Clin. Exp. Ophthalmol., vol. 234, 1996, pp 96–100.

Leake, P.A., Hradek, G.T., and Snyder, R.L., "Chronic Electrical Stimulation by a Cochlear Implant Promotes Survival of Spiral Ganglion Neurons after Neonatal Deafness", J. Comp. Neurol., vol. 412, 1999, pp 543–562.

Leake, P.A., Hradek, G.T., Rebscher, S.J., and Snyder, R.L., "Chronic Intracochlear Electrical Stimulation Induces Selective Survival of Spiral Ganglion Neurons in Neonatally Deafened Cats", Hear. Res., vol. 54, 1991, pp 251–271.

Majji, Ajit, et al.: "Long Term Histological and Electrophysiological Results of an Inactive Epiretinal Electrode Array Implantation in Dogs", Investigative Ophthalmology & Visual Science, Aug. 1999, vol. 40, No. 9, pp. 2073–2081.

Margalit, et al.: "Bioadhesives for Intraocular Use", Retina, The Journal of Retinal and Vitreous Diseases, 2000, vol. 20, No. 5, pp. 469–477.

Neely, M.D., and Nicholls, J.G., "Electrical Activity, Growth Cone Motility and the Cytoskeleton", J. Exp. Biol. vol. 198, 1995, pp 1433–1446.

Pagon, R.A., "Retinitis Pigmentosa", *Survey Opthalmol.*, vol. 33, 1988, pp 137–177.

Paton, D., Goldberg, M.F., Management of Ocular Injuries, Philadelphia, W.B. Saunders Co., 1976, pp 134–135.

Peachey, N.S., and Chow, A.Y., "Subretinal Implantation of Semiconductor–Based Photodiodes: Progress and Challenges", J. Rehabil. Res. Develop., vol. 36, No. 4, 1999, pp 1–7.

Peyman, Gholam, MD, et al.: "Subretinal Semiconductor Microphotodiode Array", Ophthalmic Surgery and Lasers, Mar. 1998, vol. 29, No. 3, pp. 234–241.

Politis, M.J., Zanakis, M.F., and Albala, B.J., "Facilitated Regeneration in the Rat Peripheral Nervous System Using Applied Electric Fields", J. Trauma., vol. 28, 1988, pp 1375–1381.

Politis, M.J., Zanakis, M.F., and Albala, B.J., "Mammalian Optic Nerve Regeneration Following the Application of Electric Fields", J. Trauma., 1988, vol. 28 pp 1548–1552.

Politis, M.J., and Zanakis, M.F., "Short Term Efficacy of Applied Electric Fields in the Repair of the Damaged Rodent Spinal Cord: Behavioral and Morphological Results", Neurosurgery, vol. 23, 1988, pp 582–588.

Politis, M.J., and Zanakis, M.F., "The Short–Term Effects of Delayed Application of Electric Fields in the Damaged Rodent Spinal Cord", Neurosurgery, vol. 25, 1989, pp 71–75.

Politis, M.J., and Zanakis, M.F., Treatment of the Damaged Rat Hippocampus with a Locally Applied Electric Field:, Exp. Brain Res., vol. 71, 1988, pp 223–226.

Reh, T.A., McCabe, K., Kelley, M.W., and Bermingham–McDonogh, O., "Growth Factors in the Treatment of Degenerative Retinal Disorders", Ciba Found. Symp., vol. 196, 1996, pp 120–131.

Rosen, J.M. "A Merger of Microsurgery and Microelectronics" in Andrade J.D. et al. (Ed.), "Artificial Organs", VCH Publishers, 1967, pp. 583–594.

*Science News*, vol. 105, No. 5, p. 105, Feb. 2, 1974.

*Science*, Jul. 1981.

Abrams, Dr. Susan B., "Implanted photodiodes could restore lost vision", *Biophotonics Research*, 1997, 2 pages.

Ando, Haruhisa, et al. "Design Consideration and Performance of a New MOS Imaging Device", *IEEE*, 1985, 6 pages.

Armington, J.C., Brigell, M., "Effects of Stimulus Location and Pattern Upon the Visually Evoked Cortical Potential and the Electroretinogram," *Intern. J. Neuroscience*, vol. 14, 1981, pp 169–178.

Baylor, D.A., Fuortes, M.G.F., "Electrical Responses of Single Cones in the Retina of the Turtle," *J. Physiol*, vol. 207, 1970, pp 77–92.

Bergmann–Schaefer, "Lehrbuch der Experimentalphysik" (Textbook of Experimental Physics), vol. II, "Electricity and Magnetism" by Prof. Dr. –Ing. H. Gobrecht, 1971, 3 pp. plus translation.

Bobsch, M.D., Joseph M. and Grosser, Ph.D., Morton "Newer Repair at the AXOM Level: A Merger of Microsurgery and Microelectronics," VCH Publishers, Inc., 1967.

Boettner, E.A., Wolter, J.R., "Transmission of the Ocular Media," *Investigative Ophthalmology*, vol . 1, 1962, pp 776–783.

Brindley, G.S., "The Site of Electrical Excitation of the Human Eye," *J. Physiol,*, vol. 127, 1955, pp 189–200.

Brindley, G.S., "Beats Produced by Simultaneous Stimulation of the Human Eye with Intermittent Light and Intermittent or Alternating Electric Current," *J. Physiol.*, vol. 164, 1962, pp 156–167.

Brown, M.G. et al., "Monolithically Integrated 1 x 12 Array of Planar InGaAs/InP Photodiodes," *Journal of Lightwave Technology*, vol. LT–4, No. 3, Mar. 1986, pp. 283–286.

Chapin, D.M., et al., "A New Silicon p–n Junction Photocell for Converting Solar Radiation into Electrical Power," Letters to the Editor, Journal of Applied Physics, vol. 25, 1954, pp 676–7.

Chow, A. Y., "Electrical Stimulation of the Rabbit Retina with Subretinal Electrodes and High Density Microphotodiode Array Implants," ARVO Abstracts, *Invest. Ophthalmol. Vis. Sci.* 199334 (Suppl), p. 835.

Curcio, C.A., Sloan, K.R., Kalina, R.E., Hendrickson, A.E., "Human Photoreceptor Topography," *J Comp. Neuro.*, vol. 292, 1990, pp 497–523.

Dawson, W.W., Radtke, N.D., "The Electrical Stimulation of the Retina by Indwelling Electrodes," *Invest. Ophthalmol. Visual Sci.*, vol. 16, 1997, pp 249–252.

Dowling, J.E., Ripps, H., Visual Adaptation in the Retina of the Skate, *J Gen Physiol.*, vol. 56, 1970, pp 491–520.

Eagle, R.C., Lucier, A.C., Bernardino, V.B., et al., "Retinal Pigment Epithelial Abnormalities in Fundus Flavimaculatus," *Ophthalmol.*, vol. 87, 1980; pp 1189–1200.

Evans, R.D., Foltz, D., and Foltz, K., "Electrical Stimulation with Bone and Wound Healing", *Clin. Podiatr. Med. Surg.*, vol. 18, 2001, pp 79–95.

Gibiliscos, S., and Sclater, N., Encyclopedia of Electronics, 2d Ed., 1990, pp. 640–645.

Fenwick, P.B.C., Stone, S.A., Bushman, J., Enderby, D., "Changes in the Pattern Reversal Visual Evoked Potential as a Function of Inspired Nitrous Oxide Concentration," *Electroencephalogr. Clin. Neurophysiol.*, vol. 57, 1984, pp 57178–183.

John B. Flynn, et al. "Total Active Area Silicon Photodiode Array", 1964, 3 pages.

Graeme, J., "Position–Sensing Photodiode Amplifiers," Ch. 10, 12 pages.

Granit, R., Helme, T., "Changes in Retinal Excitability Due to Polarization and Some Observations on the Relation Between the Processes in Retina and Nerve," *J. Neurophysiol.*, vol. 2, 1939, pp 556–565.

Hagins, W.A., Penn, R.D., Yoshikami, S., "Dark Current and Photocurrent in Retinal Rods," *J. Biophys*, vol. 10, 1970, pp 380–412.

Hergert, K., "Detectors: Expanded Photodector Choices Pose Challenges for Designers", The Photonics Design and Applications Handbook (1996).

Humayun, M.S., Propst, R.H., Hickinbotham, D., de Juan E., Jr., Dagnelie G., "Visual Sensations Produced by Electrical Stimulation of the Retinal Surface in Patients with End–Stage Retinitis Pigmentosa (RP),"ARVO Abstracts, *Invest. Ophthalmol. Vis. Sci.*, vol. 34 Suppl, 1993, p. 835.

Humayun, M., Propst R., de Juan, E., et al., "Bipolar Surface Electrical Stimulation of the Vertebrate Retina," *Arch. Ophthalmol.*, vol. 112, 1994, pp 110–116.

Kane, W.J., "Direct Current Electrical Bone Growth Stimulation for Spinal Fusion", *Spine*, vol. 13, 1988, pp 363–365.

Kataoka, S., "An Attempt Towards an Artificial Retina: 3–D IC Technology for an Intelligent Image Sensor," *Transducers '85: International Conference on Solid–State Sensors and Actuators 1985*, pp. 440–442.

Knighton, R.W., "An Electrically Evoked Slow Potential of the Frog's Retina. I. Properties of Response," *J. Neurophysiol.*, vol. 38, 1975, pp 185–197.

Lin, H–C., et al., "The Vertical Integration of Crystalline NMOS and Amorphous Orientational Edge Detector" IEEE Briefs, 1992, 3 pages.

Melen, R.D., et al., "A Transparent Electrode CCD Image Sensor for a Reading Aid for the Blind," *IEEE Journal of Solid–State Circuits*, vol. SC–9, No.2, Apr. 1974, pp. 41–48.

Narayanan, M.V., Rizzo, J.F., Edell, D., et al., "Development of a Silicon Retinal Implant: Cortical Evoked Potentials Following Focal Stimulation of the Rabbit Retina with Light and Electricity," ARVO Abstracts, *Invest. Ophthalmol. Vis., Sci.*, vol. 35 (Suppl), 1994, p. 1380.

Pagon, R.A., "Retinitis Pigmentosa," *Survey Ophthalmol.*, vol. 33, 1988, pp 137–177.

The Penguin Dictionary of Electronics, Editor: Illingworth, V., Young, C., Market House Books Ltd., 1988, pp. 410–413.

Potts, A.M., Inoue J., Buffum D., "The Electrically Evoked Response of the Visual System (EER)," *Invest. Ophthalmol Vis Sci.*, 1968; 7:269–278.

Robblee, L.S., Electrochemical Guidelines for Selection of Protocols and Electrode Materials for Neural Stimulation, Ch. 2, Renner Learning Resource Center (undated), pp 25–66.

Rovamo, J., Virsu, V., "An Estimation and Application of the Human Cortical Magnification Factor," *Exp Brain Res.*, vol. 37, 1979, pp 495–510.

Rubin, M.L., *Optics for Clinicians*, Gainsville, TRIAD Scientific Publishers, 1974, pp 119–123.

Shannon, R.V., "A Model of Safe Levels for Electrical Stimulation," *IEEE Transactions Biomed. Eng.*, vol. 39, 1992, pp 424–426.

Smith, J., "Creating a Bionic Eye", ABC News, Nov. 5, 1998, 3 pages.

Stone, J.L., Barlow, W.E., Humayun, M.S., de Juan, E., Jr., Milam, A.H., "Morphometric Analysis of Macular Photoreceptor and Ganglion Cells in Retinas with Retinitis Pigmentosa," *Arch. Ophthalmol.*, vol. 110, 1992, pp 1634–1639.

Sze, S.M., "Physics of Semiconductor Devices", $2^{nd}$ Ed., A Wiley–Interscience Publication, John Wiley & Sons, (undated).

Tasman, E., ed. *Duane's Foundations of Clinical Ophthamology*, vol. 3, Philadelphia, Lippincott, 1992; chapter 13:20–25, chapter 60:1–112.

Terr, L.I., Linthicum, F.H., House, W.F., "Histopathologic Study of the Cochlear Nucleic After 10 Years of Electrical Stimulation of the Human Cochlea," *Am. J. Otology.*, vol. 9, 1988, pp. 1–7.

Tomita, T., "Electrical Activity of Vertebrate Photoreceptor," *Q. Rev. Biophys.*, vol. 3, 1970, pp. 179–222.

Zrenner, E., et al., "The Development of Subretinal Microphotodiodes for Replacement of Degenerated Photoreceptors", *Ophthalmic Res.*, 1997, pp. 269–280.

Wen, R. et al., "Injury–Induced Upregulation of bFGF and CNTF mRNAS in the Rat Retina", *The Journal of Neuroscience*, Nov. 1995, pp. 7377–7385.

A.Y. Chow, G.A. Peyman, J. Pulido, *"Safety and Feasibility of Subretinal Artificial Silicon Retina™Retinal Prosthesis for the Treatment of Patients with Retinitis Pigmentosa"*, ARVO (The Association of Research in Vision and Ophthalmology), Abstract Issue of Annual Meeting, For Lauderdale, Florida, Apr. 29–May 4, 2001, Abstract 5042–11:11 (1 page and cover page), Published Mar. 15, 2001.

RETINAL TREATMENT METHOD

FIELD OF THE INVENTION

The invention relates to methods for providing a device or composition to a retina.

BACKGROUND OF THE INVENTION

The retina is the innermost layer of the wall of the eyeball located in the posterior segment of the eye. Developed as an outgrowth from the brain, the retina contains nervous tissue, specifically, light-sensitive cells (photoreceptors) and complex neural networks. These networks provide visual information and send impulses through the optic nerve to the brain.

Degenerative diseases of the retina, such as retinitis pigmentosa, age-related macular degeneration, and hereditary retinal degenerations cause degeneration and death of the photoreceptor cells, resulting in decreased visual function. Fortunately, even in end-stage disease, numerous neuronal cells in the inner retina survive. However, because of loss of the photoreceptors, light stimulation does not occur and the neuronal cells must be artificially stimulated to restore some degree of visual function.

The neuronal cells may be stimulated, either from the outer surface of the retina or from the so-called subretinal space. One technique for subretinal stimulation uses semiconductor microphotodiode arrays (SMA) as described in Peyman et al., *Ophthalmic Surgery and Lasers,* 1998, vol. 29, p. 234, which is expressly incorporated by reference herein in its entirety. These arrays are fabricated by standard photomask and etch techniques, and can be produced with thicknesses ranging from about 10–200 µm and sizes varying from about 0.5–5 mm in diameter. The arrays are separated into subunits, which create a pixel density of over 1000 subunits/mm$^2$. The subunits have no electrical connection; they are powered by incident light having a wavelength between 500–1100 mm. Another technique for retinal stimulation uses an electrode array to electrically stimulate the neurofiber layer of the retina. The array has 25 platinum disks arranged in a 5×5 square, as reported by Majji et al., *Investigative Ophthalmology and Visual Science,* 1999, vol. 40, p. 2073. The improved surface of the platinum disk forms a planar array of stimulating electrodes in a silicon matrix that is less than 1 mm thick. Twenty-five wires originating from the disk form a cable which extends from the array and is at least 10 cm long and 600 mm thick. To implant the array into the eye, the surface of the implant (3×5 mm) is placed over and is fixed to the retina either by mechanical fasteners such as pins or tacks, or by bioadhesives.

There are, however, several disadvantages of implanting the aforementioned types of arrays into the subretinal space. One disadvantage is that the implant may interfere with nutrition of the retina, since nutrients come partially from the choroid (the back of the retina). Fenestrations, or small openings in the array, can help to maintain nutrient accessibility to the retina. Implanting the electrode type of array over the surface of the retina has additional drawbacks. One drawback is that fixing the array over the retina is very difficult. If pins or other mechanical fasteners are used, they should penetrate the entire retina and reach the scleral wall in order to secure the array, but this increases the risk of hemorrhage from the retinal and choroidal circulation. The increased fibrous proliferation around both the fasteners and the array also causes localized scarring and traction on the retina. Another disadvantage is that electrical stimulation in the subretinal space may not adequately excite the ganglion cells and the neurofiber layer, which are located in the outer portion of the retina.

Drugs such as gancyclovir or various steroids can also be administered to the patient to attempt to prevent, halt, or alleviate the pathological process. Ocular drugs may be administered systemically, parenterally, or topically. Alternatively or additionally, the drugs may be administered in a slow release formulation.

While current methods exist for treating patients experiencing a loss in visual function due to retinal pathology, several problems still remain. Thus, additional methods to improve visual function, while decreasing or eliminating these problems, are desirable.

SUMMARY OF THE INVENTION

The invention relates to a method to provide an interventional or therapeutic substance to patients who have experienced decreased visual function due to retinal pathology or injury. The invention is also directed to a method for treating or preventing retinal pathology or injury in a mammal by surgically affixing a therapeutic or preventive substance under an internal limiting membrane in the eye to contact and stimulate the retina.

The inventive method provides the retinal stimulator substance to a mammalian eye by visualizing the internal limiting membrane of the eye, locating the retinal stimulator between the internal limiting membrane and the retina, and securing the substance under the internal limiting membrane. The method thus locates, contains, and secures a retinal stimulator substance in proximity to the retina, all by using a space provided by the internal limiting membrane in the eye.

In one embodiment, the substance is an array that is photostimulated to excite the retina. In another embodiment, the substance is an array that is electrically stimulated to excite the retina. In yet another embodiment, the substance is a drug that directly or indirectly stimulates the retina, for example, a drug that is formulated in a vehicle for slow-release delivery.

The inventive method takes advantage of the physiological placement of the internal limiting membrane in the eye. Previous surgical implant methods had removed the internal limiting membrane. However, the inventive method not only retains the internal limiting membrane, but also takes advantage of the space between it and the adjacent retinal layers to implant a therapeutic or preventative substance. In this way, non-physiological mechanical or chemical fasteners are not needed to locate and secure the implanted substance in place. Thus, there are no devices or compositions which may cause bleeding from the choroid or which may promote retinal traction originating from the cells migrating from the choroid through the mechanical pins, both of which are problems in current methods.

Another improvement using the inventive method is that the substance implanted is in direct contact with the neurofiber layer and ganglion cells of the retina. This advantageously enhances their stimulation, since the distance between the substance and its target is decreased. For example, when electrical arrays are implanted, there is enhanced qualitative and quantitative cell stimulation because the stimulus is close enough to reach ganglion cells and the neurofiber layer that is located a distance of about 10–50 µm away.

Still anther improvement is that the inventive method eliminates the need for external stimulation, as is used with currently available diode arrays.

DETAILED DESCRIPTION

Figure 1:
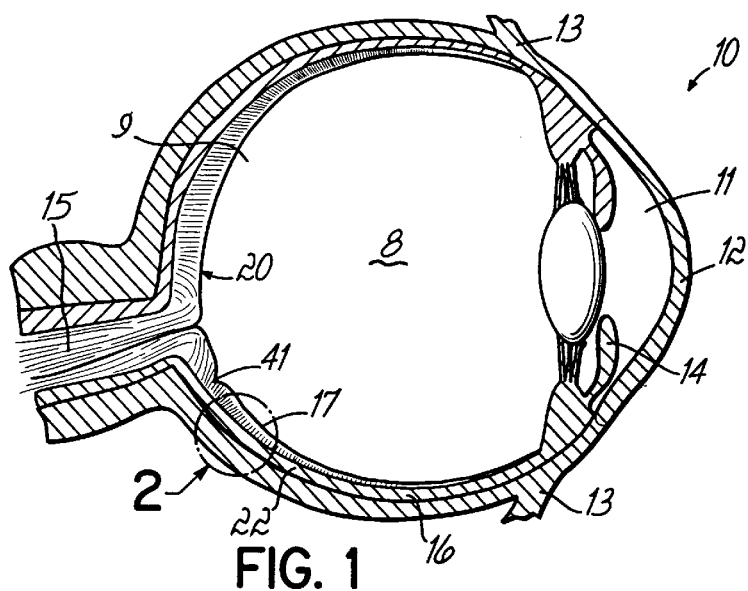
FIG. 1 is a schematic cross-sectional view of a mammalian eye.

With reference to FIG. 1, a mammalian eye 10 is shown. The locations of the vitreous cavity 8, posterior chamber 9, anterior chamber 11, cornea 12, conjunctiva 13, iris 14, optic nerve 15, sclera 16, macula lutea 17, lens 18, retina 20, ora serrata 21, and choroid 22 are illustrated.

The most sensitive portion of the retina 20 is the macula lutea 17, which is located in the center of the posterior part of the retina 20. The inner surface of the retina 20, near the border of the optic nerve 15, has a shallow round depression, the fovea 41. The fovea 41 is surrounded by the central area, distinguished by the great number of ganglion cells and by the general refinement and even distribution of the structural elements, especially the rod cells and the cone cells. About one-tenth inch inside the fovea 41 is the point of entrance of the optic nerve 15 and its central artery. At this point, the retina 20 is incomplete and forms the blind spot.

Figure 2:
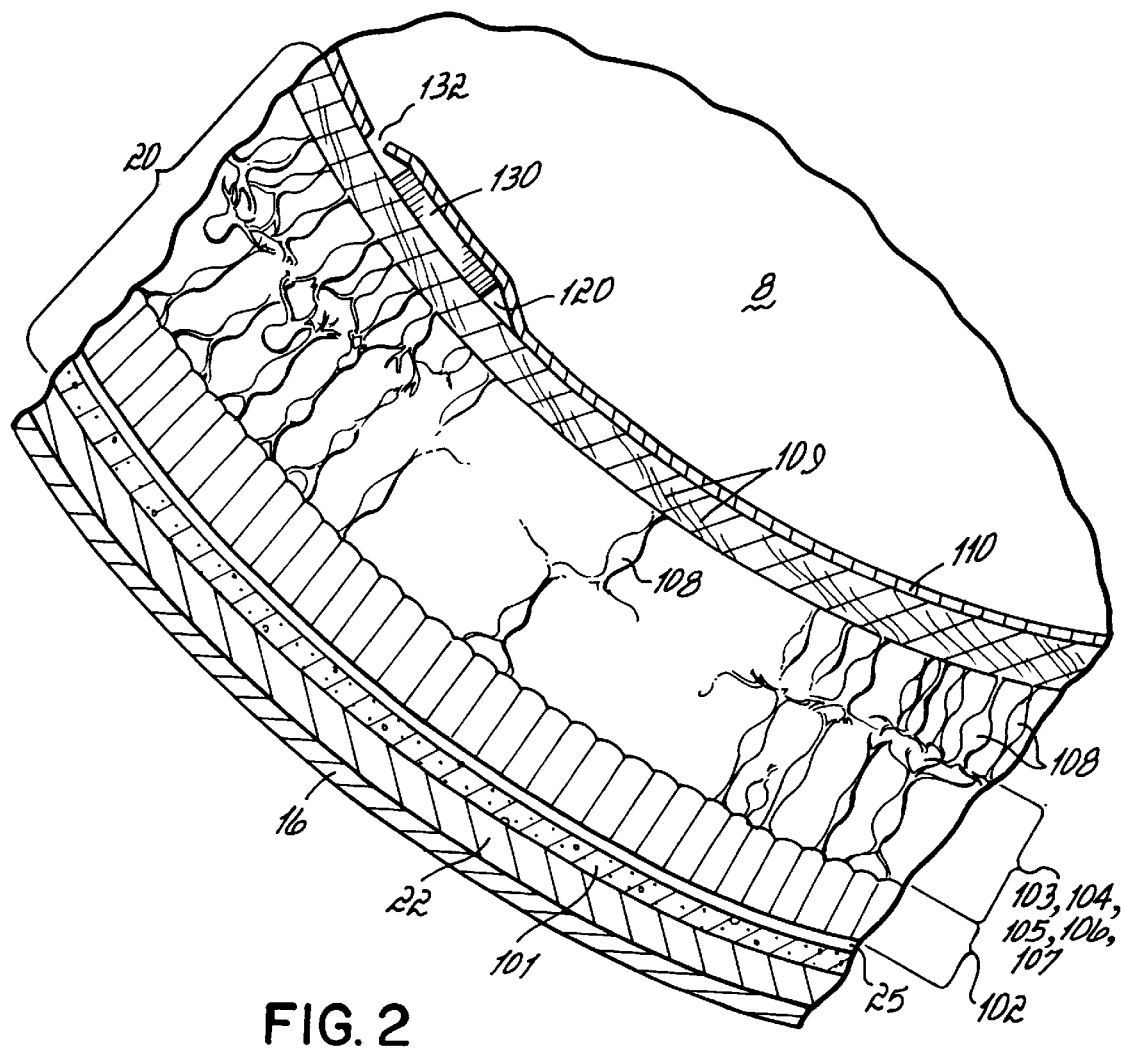
FIG. 2 is an enlarged diagrammatic illustration of the circled area 2 of FIG. 1 showing detailed retinal and choroid structures and placement of a substance using the inventive method.

With reference to FIG. 2, the retina 20 forms the innermost layer of the posterior portion of the eye and is the photoreceptor organ. The retina 20 has an optical portion that lines the inner surface of the choroid 22 and extends from the papilla of the optic nerve 15 to the ora serrata 21 anteriorly. At the papilla, where the retina 20 continues into the tissue of the nerve 15, and at the ora serrata 21, the retina 20 is firmly connected with the choroid 22. The retina 20 has ten parallel layers which are, from outside to inside, as follows: the pigment epithelium 101, photoreceptor cells (rod cells and cone cells) 102, the outer limiting membrane 103, the outer nuclear layer 104, the outer plexiform layer 105, the inner nuclear layer 106, the inner plexiform layer 107, the layer of ganglion cells 108, the layer of optic nerve fibers or neurofiber layer 109, and the so-called inner limiting membrane 110. The inner limiting membrane 110 is very thin (less than 5 µm), and normally adheres with the neurofiber layer 109 of the ganglion cells 108.

The inventive method takes advantage of the adjacent positions of the neurofiber layer 109 and ganglion cells 108 with the inner limiting membrane 110 to provide a space 120 into which a substance 130 for treating the retina 20, such as an array for electrostimulation of the retina, can be implanted and secured. The potential for and use of this space 120 in implanting an array or any other material has heretofore been unrecognized and unappreciated.

In the method, the patient is prepared for surgery, typically by providing a topical anesthesia to the eye and dilating the pupil. The eyeball is exposed and the vitreous is removed from the vitreous cavity 8 by standard techniques known to one skilled in this art. The internal limiting membrane 110 is then rendered visible to the surgeon, typically by staining. Any water soluble stain which stains the basement membrane of the internal limiting membrane 110 can be used, for example, indocyanine green, trypan blue, methylene blue, etc. The stain, for example one or two drops, is placed into the eye to allow visualization of the internal limiting membrane 110. A small incision, typically less than about 0.5 mm in diameter, is made into the internal limiting membrane 110 in the area of the macula lutea 17.

In current methods for treating a macular hole, the internal limiting membrane 110 is separated and removed using forceps.

To create a space where an array can be placed under the internal limiting membrane 110, the internal limiting membrane 110 can be separated from the retina 20 by a blunt-tipped spatula or a cannula for injection of a liquid.

In the inventive method, however, instead of cutting and removing the internal limiting membrane 110 as is routinely done, the internal limiting membrane 110 is left in place and is, in fact, used to locate the implanted substance 130. A small incision 132 is made in the internal limiting membrane 110, and the membrane 110 is then separated from the adjacent neurofiber layer 109. The substance 130 is implanted, and because the incision used for separation of the internal limiting membrane is small, the substance 130 is inserted in a secure fit. The internal limiting membrane is then repositioned over the substance 130. Furthermore, the repositioned internal limiting membrane 110 also secures the implanted substance 130 to the neurofiber layer 109 and ganglion cells 108. After the substance 130 is located and secured under the internal limiting membrane 110, the vitreous cavity 8 can be re-filled with fluid, for example, air. This fluid is subsequently absorbed and is replaced by body fluids.

In the inventive method, positioning and replacement of the internal limiting membrane 110 over the implanted substance 130 either eliminates the need for an adhesive, or allows a smaller quantity of adhesive to be used than if the internal limiting membrane was removed. If desired, however, an adhesive can also be applied to close the incision, but is not placed between the substance 130 and the retina 20. The adhesive can be, for example, a commercial fibrin sealant, autologous fibrin, Cell-Tak, photocurable glues, polyethylene glycol hydrogels, as described in Margalit et al., *Retina,* 2000, vol. 20, p. 469, which is expressly incorporated by reference herein in its entirety.

If the substance 130 implanted is an array, it may be with or without external connections. For example, an array with electrode connectors having a length of about 50 µm to about 100 µm may be implanted. An array can be of any type as is know to one of skill in this art, such as the semiconductor microphotodiode array that is described by Peyman et al., *Ophthalmic Surgery and Lasers,* 1998, vol. 29, p. 234, which is expressly incorporated by reference herein in its entirety. An array as small as 10 µm can be implanted. Alternatively, multiple small arrays, with a total size of up to about 8 mm, may be implanted. Their position can subsequently be organized and oriented magnetically. The array can be fabricated to be fenestrated, or it can be without fenestrations. The individual array can be positive-intrinsic layer-negative (PiN), mixed, negative-intrinsic layer-positive (NiP), or uniform. In the array, light absorption occurs in the front and the electricity runs to the side or the back. If electrode arrays are used, the technology described by Majii et al. is utilized, with connectors to penetrate the neurofiber layer 109 of the retina 20.

The retinal stimulator substance 130 may also be a drug. As one example, the drug may be an α-adrenergic agonist or a β-adrenergic agonist, as disclosed in U.S. Pat. No. 6,066,675 which is expressly incorporated by reference herein in its entirety. As other examples, the drug may be one or more antiinflammatory agents and/or antiproliferative agents, as is known to one skilled in the art. The drug may be implanted either alone or may be incorporated into a drug delivery system, such as a slow-release system or formulation. Examples of such systems are known to one of skill in this art and include, but are not limited to, a capsule, a bead, a liposome, a sphere, and/or a dissolvable biocompatible polymer sheet.

The inventive method provides several advantages. It eliminates the need for surgical removal of the internal limiting membrane 110. Furthermore, the inventive method takes advantage of the presence of the internal limiting membrane 110 to provide a "pocket" or space 120 for implanting the substance 130. If the substance 130 is an array, the approximation of the array to the ganglion cells 108 and the neurofiber layer 109 can better amplify the stimulation of these structures. The array thus placed requires less electrical power than is required with arrays implanted by previously known methods such as using adhesives. The signal generated, being located directly adjacent its retinal target site, is less likely to be attenuated and hence will be more efficacious. The array 130 is also securely maintained in the space 120 without the need for either mechanical fixatives, such as retinal tacks, or chemical fixatives, such as adhesives. This eliminates the problems of bleeding and/or tearing that are known to occur when mechanical fasteners such as tacks or pins are used. The inventive method also eliminates the problems associated with the use of adhesives, namely, that adhesives come off and the substance becomes dislodged from its original site of implantation, and that adhesives serve as insulators and hence interfere with transmission of an electrical signal from an array to the retina 20.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method for providing a substance to a mammalian eye having an internal limiting membrane, the method comprising:
    visualizing the internal limiting membrane of the eye;
    locating the substance between the internal limiting membrane and the retina; and
    using the internal limiting membrane to secure the substance.

2. The method of claim 1 wherein the substance comprises a drug.

3. The method of claim 1 wherein the substance comprises a device.

4. The method of claim 3 wherein the device comprises at least one array for electrostimulation of the retina.

5. The method of claim 4 wherein the device has external connectors.

6. The method of claim 1 wherein the substance is in a delivery vehicle.

7. The method of claim 6 wherein the delivery vehicle is selected from the group consisting of a capsule, a bead, a liposome, a sphere, a dissolvable biocompatible polymer sheet, and combinations thereof.

8. The method of claim 6 wherein the delivery vehicle provides slow-release drug delivery.

9. A method for effecting treatment of a retina in a mammal comprising providing a substance between an internal limiting membrane and the retina to contact the retina and stimulate retinal cells to effect treatment.

10. The method of claim 9 wherein the treatment effected is for a condition selected from the group consisting of retinitis pigmentosa, macular degeneration, a degenerative retinal disease, and combinations thereof.

11. The method of claim 9 wherein the substance comprises at least one semiconductor microphotodiode array.

12. The method of claim 9 wherein the substance comprises at least one electrode array.

13. The method of claim 9 wherein the substance comprises a vehicle containing a drug.

14. The method of claim 13 wherein the drug is selected from the group consisting of an α-adrenergic agonist, a β-adrenergic agonist, an antiinflammatory agent, an antiproliferative agent, and combinations thereof.

15. The method of claim 9 wherein retinal cells stimulated are selected from the group consisting of photoreceptor cells, ganglion cells, neurofiber cells, and combinations thereof.

16. A method for enhancing vision in a patient having decreased vision due to retinal pathology or injury comprising locating a retinal stimulator substance between an internal limiting membrane and the retina, the substance capable of stimulating the retina to enhance visual function.

17. The method of claim 16 wherein the substance comprises a photostimulated semiconductor microphotodiode array.

18. The method of claim 17 further comprising providing a light source to stimulate the array.

19. The method of claim 16 wherein the substance comprises an electrically stimulated electrode array.

20. The method of claim 19 further comprising providing an electrical source to stimulate the array.

21. The method of claim 16 wherein the patient has a retinal pathology selected from the group consisting of retinitis pigmentosa, macular degeneration, a retinal degenerative disease, and combinations thereof.

22. A method for effecting treatment of a retina in a mammal comprising providing retinal chemical stimulator between an internal limiting membrane and the retina to contact the retina and stimulate retinal cells to effect treatment.

23. The method of claim 14 wherein the drug affects retinal degeneration.

24. The method of claim 14 wherein the drug is regenerative.

25. The method of claim 1 wherein the substance comprises a drug and a device.

26. A method for effecting treatment of a retina in a mammal comprising providing at least one connectionless array between an internal limiting membrane and the retina to contact the retina and stimulate retinal cells to effect the treatment.

27. The method of claim 26, wherein the at least one connectionless array comprises at least one photostimulated array.

28. The method of claim 27, wherein the at least one photostimulated array comprises at least one semiconductor microphotodiode array.

29. The method of claim 1, wherein the substance comprises at least one connectionless array.

30. The method of claim 29, wherein the at least one connectionless array comprises at least one photostimulated array.

31. The method of claim 30, wherein the at least one photostimulated array comprises at least one semiconductor microphotodiode array.

* * * * *

UNITED STATES PATENT AND TRADEMARK OFFICE
CERTIFICATE OF CORRECTION

PATENT NO. : 7,037,943 B2
APPLICATION NO. : 09/832269
DATED : May 2, 2006
INVENTOR(S) : Gholam Peyman and Alan Y. Chow It is certified that error appears in the above-identified patent and that said Letters Patent is hereby corrected as shown below:

On the title page item (75), should read
Gholam Peyman, New Orleans, LA
Alan Y. Chow, Wheaton, IL.

Signed and Sealed this

Twenty-second Day of August, 2006

JON W. DUDAS
*Director of the United States Patent and Trademark Office*